United States Patent [19]
Salvati et al.

[11] Patent Number: 5,373,317
[45] Date of Patent: Dec. 13, 1994

[54] CONTROL AND DISPLAY SECTION FOR BORESCOPE OR ENDOSCOPE

[75] Inventors: Jon R. Salvati; Fred C. Cope, both of Skaneateles; Dominick Danna, Syracuse; Michael C. Stone, Skaneateles; Raymond A. Lia, Auburn; Gary L. Rink, Jordan; Craig S. Whitaker, Marietta, all of N.Y.

[73] Assignee: Welch Allyn, Inc., Skaneateles Falls, N.Y.

[21] Appl. No.: 68,144

[22] Filed: May 28, 1993

[51] Int. Cl.⁵ ............................................. H04N 7/18
[52] U.S. Cl. .......................................... 348/65; 348/76
[58] Field of Search ................... 358/98; 348/65, 71, 348/76; 244/3.11; 200/6 A

[56] References Cited

U.S. PATENT DOCUMENTS

| | | |
|---|---|---|
| 4,253,447 | 3/1981 | Moore et al. |
| 4,261,344 | 4/1981 | Moore et al. |
| 4,491,865 | 1/1985 | Danna et al. |
| 4,503,842 | 3/1985 | Takayama. |
| 4,739,128 | 4/1988 | Grisham .......................... 200/6 A |
| 4,941,456 | 7/1990 | Wood et al. ........................ 358/98 |
| 5,034,888 | 7/1991 | Uehara et al. ..................... 358/98 |
| 5,042,743 | 8/1991 | Carney ............................ 244/3.11 |
| 5,060,632 | 10/1991 | Hibino et al. ..................... 358/98 |
| 5,070,401 | 12/1991 | Salvati et al. .................... 358/98 |
| 5,230,059 | 7/1993 | Nielsen et al. ................... 395/800 |
| 5,243,967 | 9/1993 | Hibino ............................. 348/65 |

Primary Examiner—Tommy P. Chin
Assistant Examiner—Emil P. Lenchak
Attorney, Agent, or Firm—Harris Beach & Wilcox

[57] ABSTRACT

A control handle and viewing screen assembly combines video monitor and remote steering control for a borescope steering section. A joystick or similar device controls the steering section when an inspection mode is employed. In a second or freeze-frame mode the joystick is used to move a cursor on the screen or to carry out a computation function. Steering servo motors can be positioned distally for balance.

18 Claims, 5 Drawing Sheets

CONTROL AND DISPLAY SECTION FOR BORESCOPE OR ENDOSCOPE

BACKGROUND OF THE INVENTION

The present invention relates to borescopes or endoscopes, and is more particularly directed to a consolidated control handle and viewing screen for a video borescope or endoscope or the type having a remotely articulated tip.

Borescopes or endoscopes of this type have a flexible elongated insertion tube, which can have a miniature video camera situated within its distal tip, or alternatively can have a fiber optic imaging system, and a video camera positioned at a proximal end of the unit. A borescope is an industrial type device intended for inspection of inaccessible areas of a complex machine or device, such as the tubes of a boiler or the vanes of a gas turbine. An endoscope is a medical device which can be inserted into a body cavity, e.g. the esophagus or colon, for diagnostic or surgical purposes. A laparoscope is a specific type of endoscope in which the insertion tube enters the body through an incision. The laparoscope usually has a rigid insertion tube which can have an articulated portion near its distal tip.

The borescope or endoscope has a control section at the proximal end of the insertion tube for remote bending or flexing of the distal articulation section. Frequently, the articulation section is cable actuated, and there are two pairs of steering cables that extend through the insertion tube from the control section to the distal articulation section. In one typical configuration, there is a rack and pinion mechanism in the control section which is actuated by a pair of steering knobs for manipulating the steering of the distal tip in two crossed planes disposed at ninety degrees. These are typically in the X direction (corresponding to left and right movement) and the Y direction (corresponding to up-and-down movement). One or both pairs of cables are differentially displaced for moving the tip of the borescope or endoscope to facilitate visual inspection of an object.

Light for illumination is conveyed from an external light source over a fiber optic bundle that passes through the insertion tube.

Endoscopes and borescopes of this general type have been described in Moore et al. U.S. Pat. No. 4,253,447; Moore et al. U.S. Pat. No. 4,261,344; and Danna et al. U.S. Pat. No. 4,491,865.

A recent proposal has been to employ joystick controlled motor devices to move the two pairs of steering cables, where the motor drives are incorporated in the housing of the control section. One such arrangement is proposed in U.S. Pat. No. 4,503,842.

In a typical video type borescope or endoscope, an umbilical tube extends proximally from the control section and connects to a video processor and video monitor. According to the specific system, the monitor can provide a full color image or a black-and-white image of the object in the viewing field of the video camera. The monitor is either incorporated into the video processor or provided in a separate cabinet. This aspect limits the portability of the system by requiring the monitor to be carried, and space needs to be provided for it in the carrying case. Moreover, it is often inconvenient for the operator to use a conventional monitor, because he or she must continually direct his or her attention back and forth between the monitor and the control handle.

A technique of measuring objects in the field of view of the viewing camera has been describe in Salvati et al. U.S. Pat. No. 5,070,401. In that system, measurements of the object, e.g., its width, slant length, and depth, can be calculated from information on the screen without need to impose a scale next to the object to be measured. This technique requires an electronic system for automatically carrying out the necessary measurements, based upon pre-programmed algorithms. The system is operated from a keyboard in conjunction with a joystick, mouse, trackball or similar device to move a marker or cursor on the screen. These control devices, namely the keyboard and the joystick device, are also separate elements and have to be located at some distance from the control handle. This makes it somewhat inconvenient to carry out the measurement technique.

OBJECTS AND SUMMARY OF THE INVENTION

It is an object to provide a borescope or endoscope which overcomes the above-noted drawbacks.

It is another object to provide a borescope or endoscope having a steering control mechanism and a viewing screen conveniently combined in a hand-held control unit.

It is a further object to provide a borescope or endoscope, in which a joystick, trackball, or other manually actuable device can serve a dual function; in a first mode controlling the bending of the endoscope or borescope articulation neck; and in a second mode controlling the cursor position of the viewing screen.

A still further object of the invention is to provide a combined control handle and viewing screen which is well balanced and adequately designed for one-hand operation.

According to an aspect of this invention, a borescope or endoscope is provided with an elongated flexible insertion tube including a viewing head at its distal tip and a remotely steerable articulation section adjacent the distal tip. The articulation section is controllably deflectable in the X and Y directions, that is side-to-side and up-and-down.

A control handle coupled to the proximal end of the insertion tube serves combined functions of controlling the bending of the articulation section and of presenting a video display of an image in view of the viewing head. The later function is served by a miniature viewing screen, such as a color LCD screen, mounted within the housing of the control handle.

A manually actuable device, e.g., a joystick, contained in the control handle housing, is movable in X and Y orthogonal directions and provides respective X and Y output values. Within the control handle housing there are respective X and Y motive devices, e.g. first and second servo motors or stepper motors, which are connected to the steering cables that extend through the flexible insertion tube up to the bending section. These motive devices produces differential movement of the respective cable pair in response to the X and Y values produced by the joystick or other manually actuable device.

At least one keyswitch, and favorably a row of keyswitches is provided adjacent the viewing screen. A predetermined one of these can serve a mode switchover function.

An electronic control circuit within the housing, which can include a microprocessor, serves a computation function and generates a cursor which is visible on the screen and can be moved, e.g. by manipulating the joystick or other device. The electronic control circuit also includes means to carry out a mode changeover function responsive to actuation of the predetermined one of the keyswitches. In the first mode the X and Y values are applied from the manually actuable device to control the movement of the servo motors or other such X and Y motive means such that manual movement of the joystick or other device procedures a corresponding movement of the articulation section, e.g. to move the viewing head into position to see a target. In the second mode the X and Y values are applied to the electronic control circuit, and are cut off from the servo motors. In this mode movement of the joystick or other device produces a corresponding cursor movement on screen, but does not affect the articulation section.

In a preferred embodiment, the outputs of the joystick device are converted to digital values.

The keyswitch used to effect mode changeover is preferably a freeze-frame switch which is also operative to command the electronic control circuit to store a frame of the video signal and continuously present the stored video frame to the viewing screen when the mode change-over function selects the second mode.

The electronic circuitry for carrying out the measurement functions can be contained in a remote unit or can be integrated within the control handle.

Other functions such as brightness control can involve other keyswitches.

The above and many other objects, features, and advantages of this invention will become apparent from the ensuing detailed description of one preferred embodiment, which should be read in conjunction with the accompanying Drawing.

DETAILED DESCRIPTION OF THE PREFERRED EMBODIMENT

Figure 1:
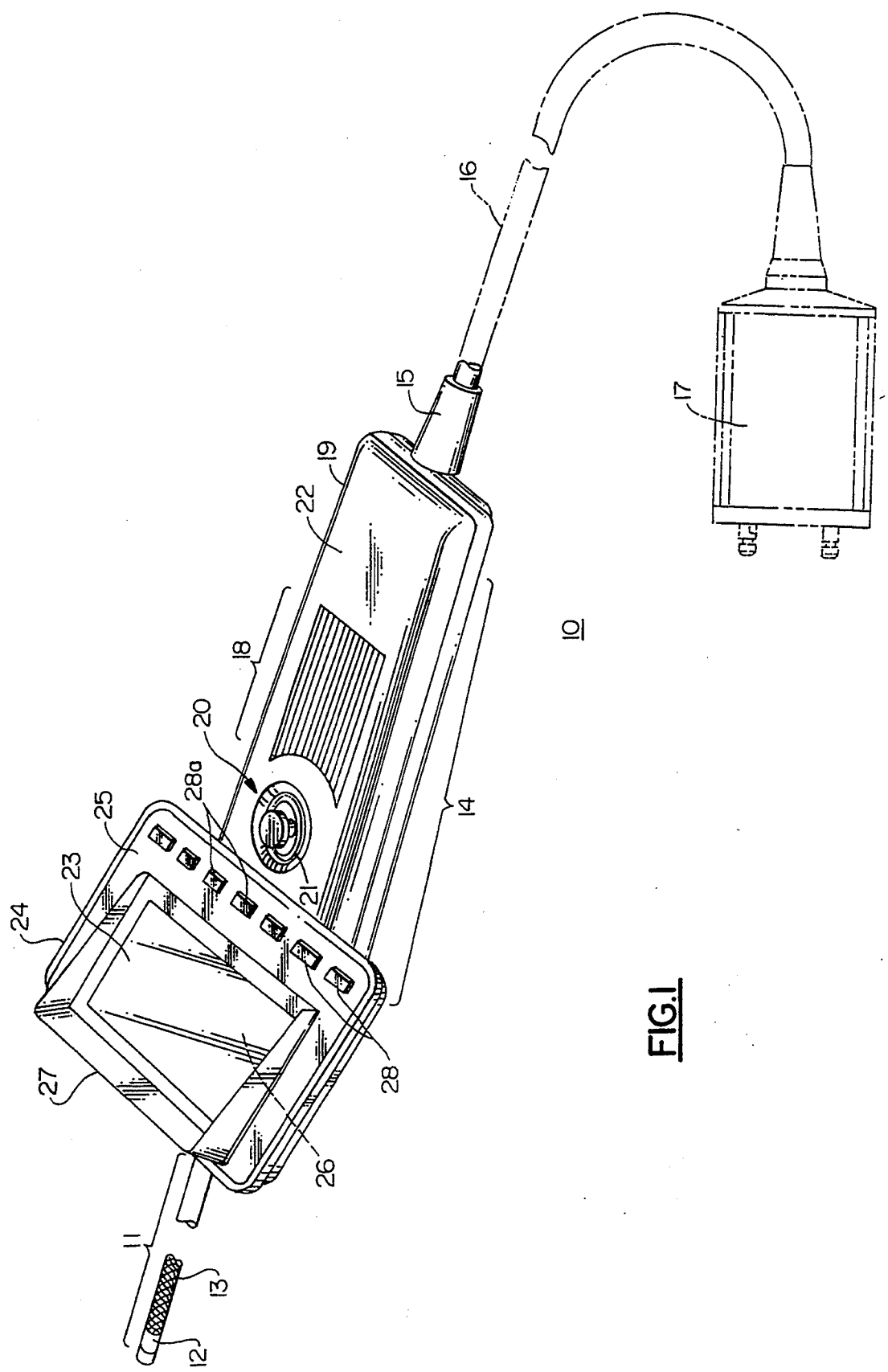
FIG. 1 is a perspective view of a borescope with a combined assembly control handle and video display assembly according to one preferred embodiment of the invention.

With reference to the Drawing and initially to FIG. 1, a borescope 10 is shown with an elongated flexible insertion tube 11 which can be inserted into an opening in a machine or other complex object to inspect a target inside it. A viewing head 12 is disposed at the distal tip of the insertion tube and a bidirectional or X-Y articulation section 13 is disposed adjacent the viewing head. The proximal end of the insertion tube 11 terminates in a combined control handle and viewing screen assembly 14.

A strain relief 15 on the proximal end of the assembly 14 connects to a flexible umbilical 16 which has a connector processor module 17 disposed at its proximal end. The module 17 contains video processing circuitry matched to the video camera which is incorporated into the viewing head 12. The processor plugs into a power supply and light source (not shown) which provides appropriate DC levels for the borescope 10 and also provides light which is carried on a fiber optic bundle that passes through the umbilical 16, the control handle assembly 14 and the insertion tube 11 to the head 12, where it emits light for illuminating an object in the viewing field of the head 12. This type of connector or coupler module is described, for example, in U.S. patent application Ser. No. 07/944,129 filed Sep. 11, 1992, having a common assignee herewith.

Figure 2:
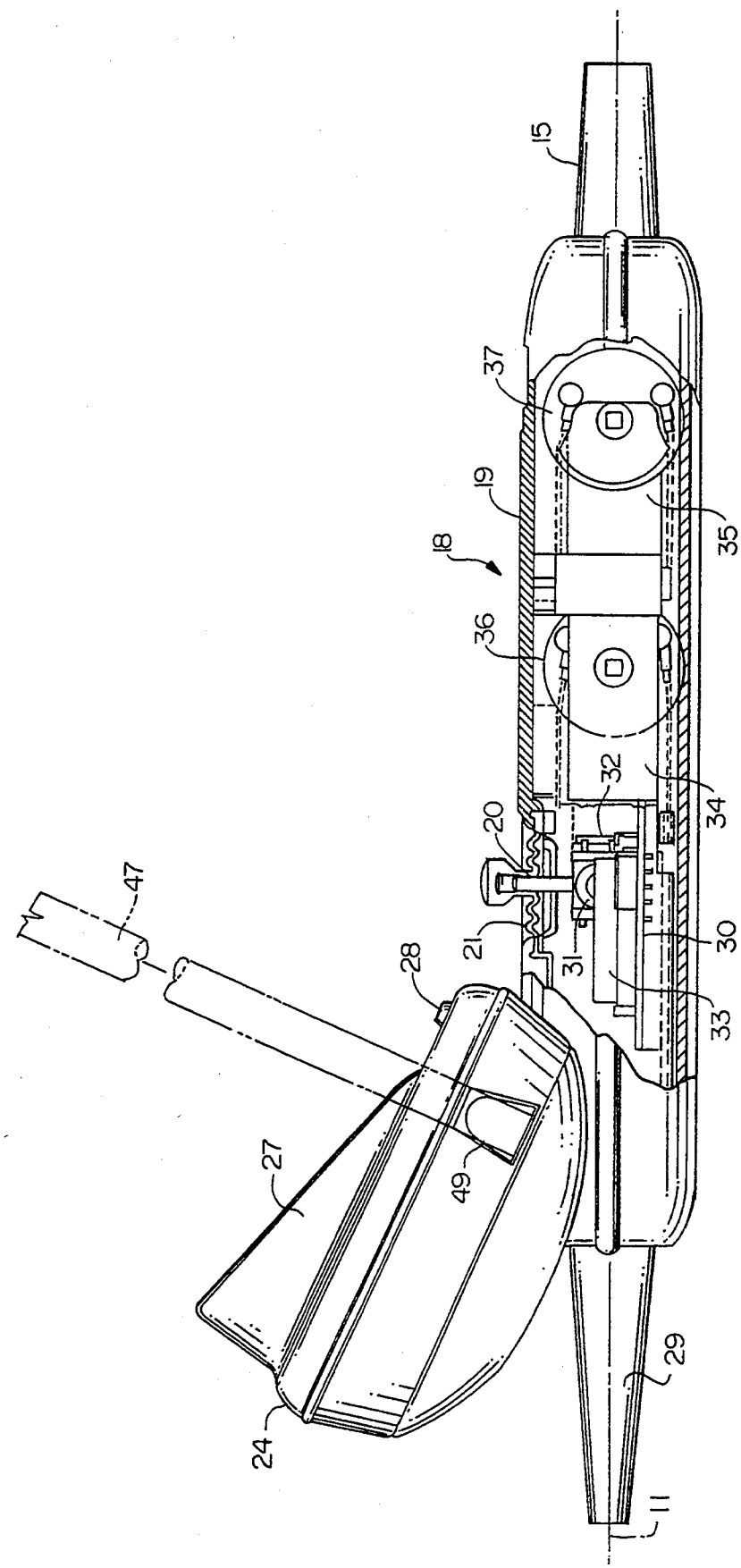
FIG. 2 is a side elevation of the combined control handle and video/display assembly, partly cut away to show the interior of the steering control portion thereof.

With reference also now to FIG. 2, the combined control handle and viewing screen assembly 14 has a proximal handle portion which is elongated in the fore-and-aft direction. A housing 19 has a joystick device 20 contained in an elastomeric boot 21 mounted in top wall 22 of the housing 19.

Distally of the joystick device 20 is a small, full-color viewing screen 23. In this example the screen 23 is a liquid crystal display (LCD) type screen, with fluorescent backlighting. This screen 23 is mounted within a distal video monitor portion 24 of the assembly 14. Here, an oblong top portion 25 of the housing 19 has a glass plate or cover 26 over the screen 23, and a hood 27 surrounding at least top and side edges to reduce background glare. A hood insert (not shown) can fit within this to permit viewing of the screen in daylight or other bright ambient conditions.

A row of keyswitches 28 is provided on the oblong top portion 25 adjacent the screen 23. Some of these can be used to adjust brightness up or down when the probe is used in a primary or inspection mode. Among the keyswitches is a freeze-frame keyswitch 28a which switches the unit over from the inspection mode to a second, freeze-frame mode. In that mode, others of the keyswitches are actuated to carry out various measurements. A forward strain relief 29 extends beneath the distal video monitor portion 24 and holds the proximal end of the insertion tube 11.

As is also shown in FIG. 2 the joystick device 20 is mounted on a circuit board 30 within the housing 19 and has an associated X-axis variable resistance 31 and Y-axis variable resistance 32. A microprocessor 33 is also mounted on the board 30.

Positioned within the housing 19 of the proximal handle portion, and to the proximal side of the joystick device, are X and Y servo motors 34 and 35 which are operatively coupled to respective X and Y pulleys 36 and 37. The pulleys are connected in known fashion with respective X and Y cable pairs that run through the insertion tube 11 to the articulation section 13. The pulleys 36, 37 produce differential displacement in the respective cable pairs. This flexes the articulation section 13 in the sideways direction (left to right) or the up-and down direction. In the inspection mode, the joystick device 20 is operatively coupled to the servo motors 34 and 35, so that movement of the joystick 20 produces a corresponding movement of the articulation section 12.

Figure 3:
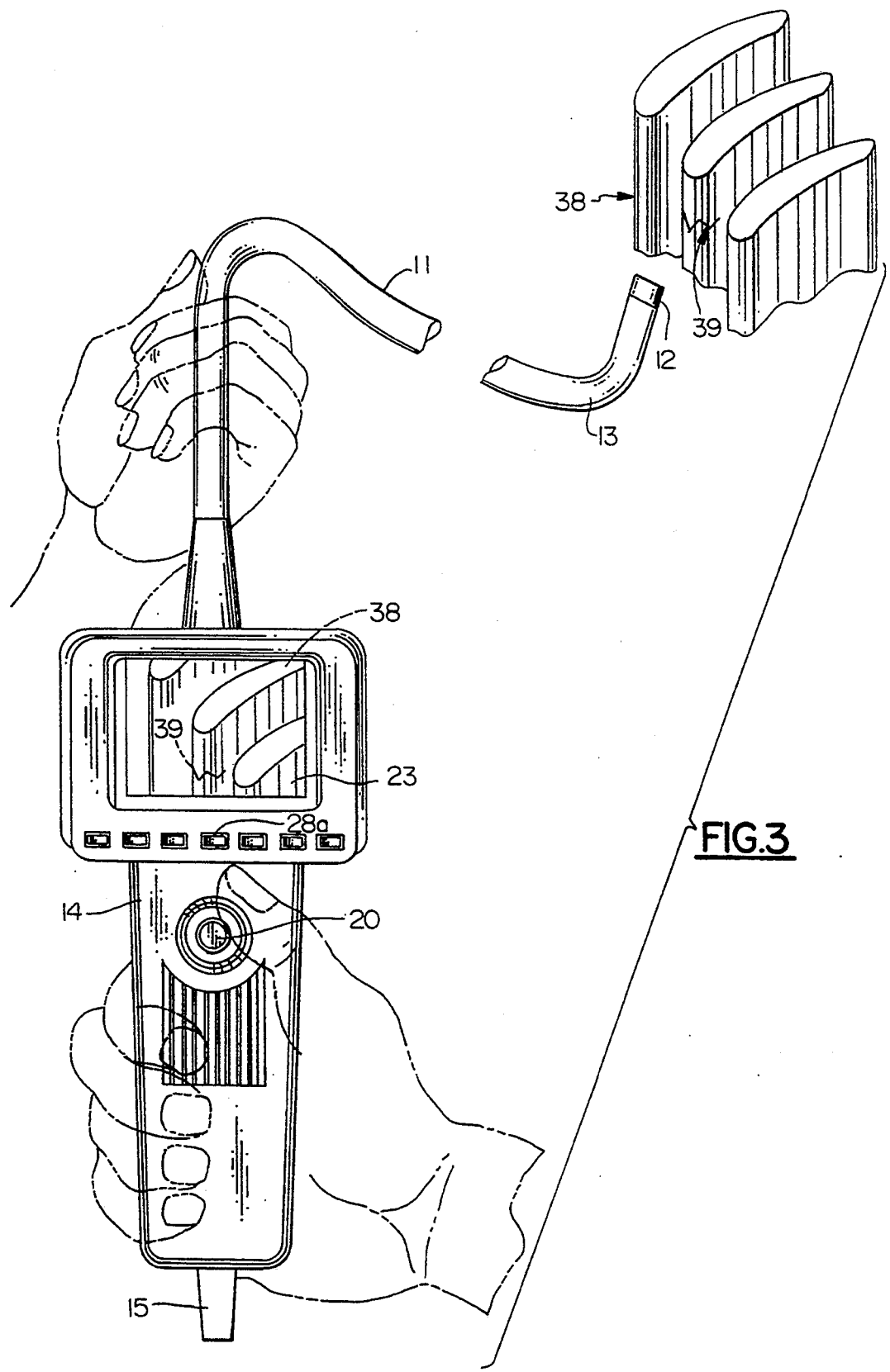
FIGS. 3 and 4 are perspective view to illustrate and explain first and second operating modes of the borescope of this embodiment.

The operation of the borescope 10 of this embodiment can be explained with reference to FIGS. 3 and 4. FIG. 3 shows the borescope being used in an inspection mode with an operator's left hand holding the control handle and viewing screen assembly 14 and the right hand feeding the insertion tube 11 into apparatus to be inspected. In this example the apparatus can be a jet engine or similar turbine, with the target being a row of turbine vanes 38. Furthermore, in this example a crack or irregularity 39 has appeared on one of the vanes 38, and the operator needs to investigate the same, not only to view its appearance, but also to measure its length and depth.

As shown in FIG. 3, the operator can manipulate the joystick device 20, here using the thumb of the same hand that is holding the assembly 14, to steer the viewing head 12 as need be for an optimal position to view the crack 39 on the viewing screen 23. When the operator has achieved a satisfactory image of the crack 39, he or she actuates the freeze-frame keyswitch 28a, which causes the microprocessor 33 to switch over to a freeze-frame mode.

Figure 4:
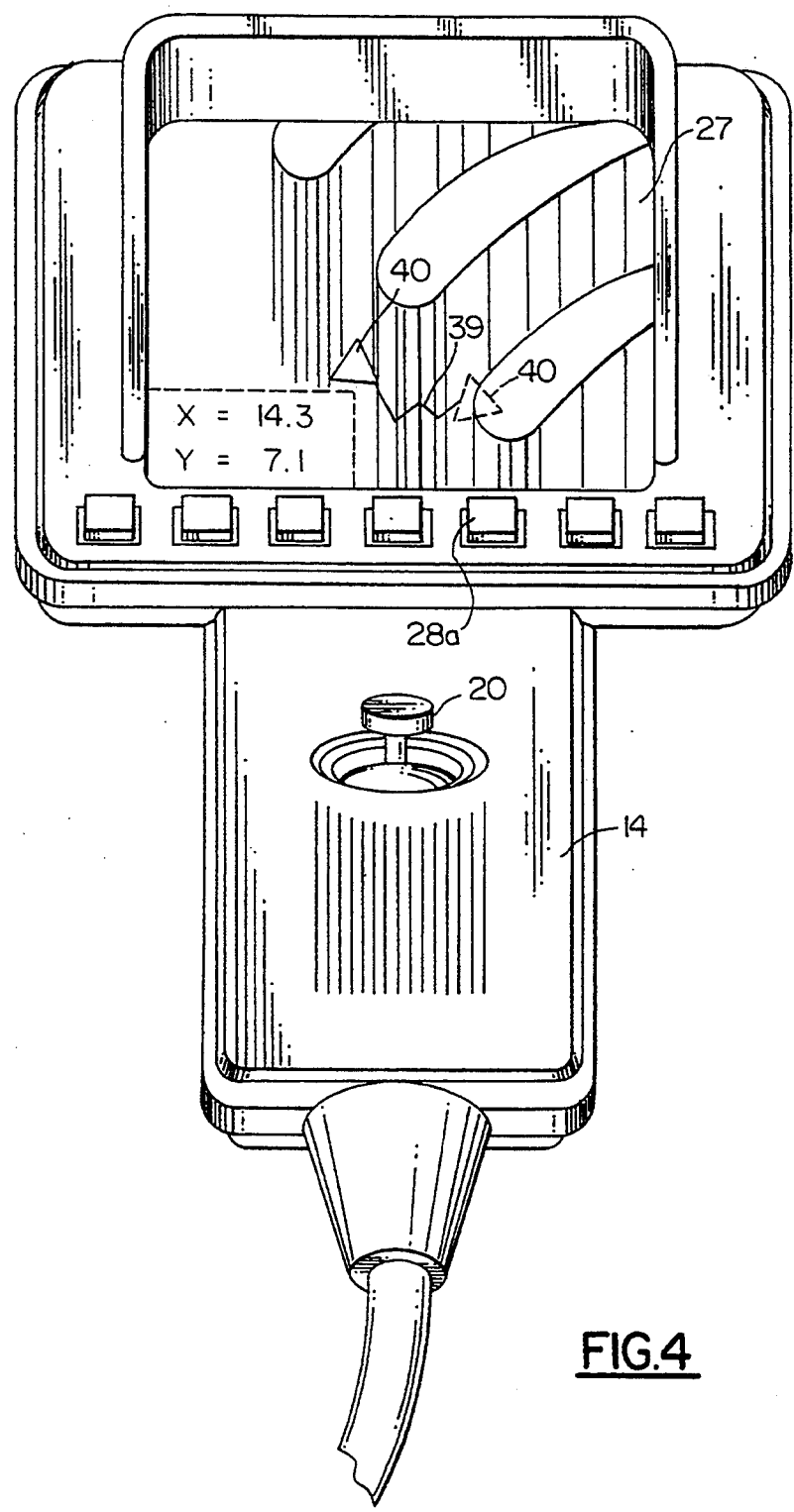

In the second, or freeze-frame mode, as illustrated in FIG. 4, a single frame of the video signal that represents the target 38 is seized and stored, and is fed continuously to the video screen 23. In the freeze-frame mode, the joystick device 20 is operatively disconnected from the servo motors 34, 35 (these are maintained at the last position achieved in the inspection mode), and is operatively coupled, through the microprocessor 33, to the viewing screen 23. In this mode, the operator manipulates the joystick device 20, in combination with the actuation of the remaining keyswitches 28, to carry out analysis and measurement functions.

As shown in FIG. 4, in the freeze-frame mode a cursor 40 appears on screen. The joystick device 20 is manipulated to move the cursor 40 about on the image reproduced on the screen 23, e.g. from one end of the crack 30 to the other. A measurement algorithm contained in the microprocessor computes the desired quantity, such as crack length. The computation itself can be carried out in a manner as described, e.g. in U.S. Pat. No. 5,070,041.

When the desired computations are completed, the operator can depress the freeze-frame keyswitch 28a a second time. This will return the probe to its inspection mode, and the joystick device is again operatively coupled to the servo motors 34, 35 to control the remote articulation of the section 13.

The dual function of the joystick device as described here avoids the need for a second similar device and eliminates the need for a separate keypad.

Figure 5:
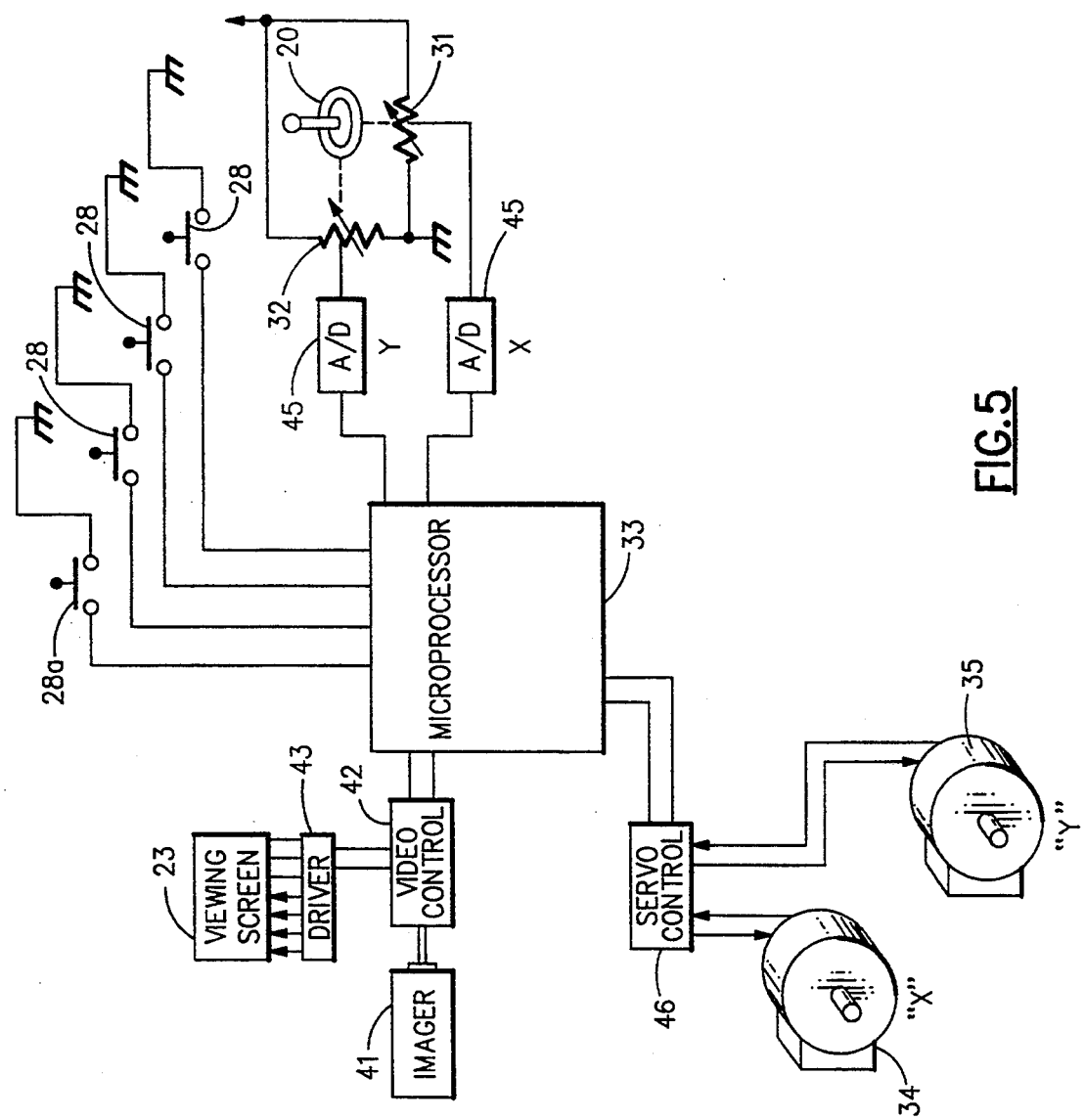
FIG. 5 is a schematic circuit block diagram of the circuitry of this embodiment.

FIG. 5 is a simplified schematic diagram of the borescope circuitry to facilitate an understanding of the above-described embodiment.

A CCD imager 41 or similar device, contained within the viewing head 12 provides a signal representing the target to the processor module which converts the signal to a monitor-ready color video signal. This is furnished to a driver circuit 43 that produces a replica of the target on the screen 23. A video control circuit 42 is interposed between the imager 41, driver circuit 43 and microprocessor 33. The keyswitches 28, including the freeze-frame keyswitch 28a, are operatively coupled to inputs of the microprocessor 33.

The variable resistances 31 and 32 that are associated with the joystick device 20 produces analog voltage levels that vary respectively with the position of the device 20 in the X or side-to-side direction and the Y or up-and-down direction. These analog levels are supplied to respective X and Y analog-to-digital converters 44, 45 which in turn furnish corresponding digital values to the microprocessor 33. In a practical embodiment, the converters 44 and 45 can be incorporated into the microprocessor 33.

In the inspection mode, these digital values are furnished by the microprocessor to a servo control circuit 46 which operates the servo motors 34 and 35. In the freeze-frame mode, the digital values at the time of mode change are stored and continuously furnished to the servo control circuit 46. The digital values from converters 44, 45 which represent actual joystick positions are used in the microprocessor for other purposes, such as cursor position on screen, or to move through an on-screen menu.

Returning now to FIG. 2, a neck strap 47 is shown in ghost, with a wedge shaped connector 48 that fits into an undercut notch 49 on the side of the monitor portion 24 of the housing. A similar connector 48 and notch 49 are provided on the other side. The neck strap is removable, and reduces operator fatigue from holding the assembly 14. The placement of the servo motors 34 and 35 proximally within the handle portion 18 lets them serve as a counterpoise for the distal monitor portion 24. This provides a balanced construction, with a center of gravity near the location of the joystick device 20.

In this embodiment, servo motors are employed for remote bending of the articulation section. In other embodiments, stepper motors could be employed. As a further alternative, fluid controlled bending could be used, as described in U.S. Pat. No. 4,794,912, or in U.S. Pat. No. 5,018,506.

The invention could also be employed with a borescope or endoscope that is steerable in one plane only (i.e., only the X-direction).

While this invention has been described in detail with reference to one preferred embodiment of the invention, it should be understood that the invention is not limited to that precise embodiment. Rather, many modifications and variation will be apparent to those skilled in the art without departing from the scope and spirit of the invention as defined in the appended claims.

What is claimed is:

1. A borescope or endoscope comprising an elongated flexible insertion tube including a video imaging device on its distal tip for producing a video signal representing an image of a target within its viewing field; and a remotely steerable articulation section adjacent said distal tip of said articulation section being deflectable in at least one plane and a control handle and viewing unit coupled to a proximal end of said insertion tube and including a control handle housing; a viewing screen incorporated onto said control handle housing for displaying an image of said target within the viewing field of said video imaging device; a manually actuable device on said control handle housing movable in at least one direction including means providing an output value in response to the amount and direction of movement of said manually actuable device; motive means within said control handle housing, responsive to said output value, for exerting a steering force on said articulation section to bend same; at least one keyswitch on said control handle housing; electronic control circuit means within said control handle housing coupled to said at least one keyswitch and said viewing screen, including computation means for computing characteristics of the target displayed on the screen, and means for generating a cursor which is visible on said viewing screen and movable thereon; and including mode switchover means responsive to a selected one of said at least one keyswitch between a first mode in which said output value is applied to control said motive means such that movement of said manually actuable device produces a corresponding movement of said articulation section, and a second mode in which said output value is applied to said electronic control circuit means such that movement of said manually actuable device produces a corresponding movement of the cursor on said screen, but does not affect the articulation section.

2. The borescope or endoscope of claim 1, wherein said control handle housing includes a distal portion enclosing said viewing screen and a proximal handle portion containing said manually actuable device and said motive means.

3. The borescope or endoscope of claim 2, wherein said motive means are positioned at a proximal end of said proximal handle portion to serve as a counterpoise for said viewing screen.

4. The borescope or endoscope of claim 2 wherein said viewing screen includes an LCD video display.

5. The borescope or endoscope of claim 1 wherein said manually actuable device includes a joystick having a handle movable in two degrees of freedom, and respective variable resistance devices providing output levels that vary with position of said handle in respective orthogonal directions.

6. The borescope or endoscope of claim 5 wherein said manually actuable device further includes respective analog-to-digital converter means coupled to said variable resistance devices to produce respective X and Y digital values corresponding to said output levels.

7. The borescope or endoscope according to claim 1 wherein said at least one keyswitch includes a freeze-frame keyswitch on said control handle housing operatively coupled to said electronic control circuit such that when the freeze-frame keyswitch is actuated, the electronic control circuit is operative to store a frame of said video signal and continuously present said frame of said video signal to said viewing screen and at the same time said switchover means is set over into its second mode.

8. The borescopes or endoscope according to claim 7 wherein said at least one keyswitch includes a plurality of additional keyswitches operative to furnish respective computation function commands to said electronic control circuit computation means.

9. The borescope or endoscope according to claim 8 wherein said control handle housing includes a distal portion enclosing said viewing screen and a proximal handle containing said manually actuable device, and said keyswitches are arranged on said distal portion of said control handle housing adjacent said viewing screen.

10. A borescope or endoscope comprising an elongated flexible insertion tube including a video imaging device on its distal tip for producing a video signal representing an image of a target within its viewing field; and a remotely steerable articulation section adjacent said distal tip of said articulation section being deflectable in one plane; and a combined control handle and viewing unit coupled to a proximal end of said insertion tube and including a control handle housing; a viewing screen affixed on said control handle housing for displaying an image of said target within the viewing field of said video imaging device; a manually actuable device on said control handle housing, movable in at least one direction, including means providing respective output values in response to the amount and direction of movement of said manually actuable device; respective motive means within said control handle housing, responsive to said output values, for exerting steering forces on said articulation section to bend same in a respective at least one direction in said plane; electronic control circuit means within said control handle housing coupled to said motive means and operative in a first mode in which said values are applied to control said motive means such that movement of said manually actuable device produces a corresponding movement of said articulation section.

11. The borescope or endoscope of claim 10, wherein said control handle housing includes a distal portion enclosing said viewing screen and a proximal handle portion containing said manually actuable device and said motive means.

12. The borescope or endoscope of claim 11, wherein said motive means are positioned at a proximal end of said proximal handle portion to serve as a counterpoise for said viewing screen.

13. The borescope or endoscope of claim 11 wherein said viewing screen includes an LCD video display.

14. The borescope or endoscope of claim 10 wherein said manually actuable device includes a joystick having a handle movable in two degrees of freedom, and respective variable resistance devices providing output levels that vary with position of said handle in respective orthogonal directions.

15. The borescope or endoscope of claim 14 wherein said manually actuable device further includes respective analog-to-digital converter means coupled to said variable resistance devices to produce respective digital values corresponding to said output levels.

16. The borescope or endoscope according to claim 10 including a freeze-frame keyswitch on said control handle housing operatively coupled to said electronic control circuit such that when the freeze-frame keyswitch is actuated, the electronic control circuit is operative to store a frame of said video signal and continuously present said frame of said video signal to said viewing screen and at the same time said motive means are disabled from deflecting the articulation section.

17. The borescopes or endoscope according to claim 16 wherein said at least one keyswitch includes a plurality of additional keyswitches operative to furnish respective computation function commands to computation means within said electronic control circuit.

18. The borescope or endoscope according to claim 17 wherein said control handle housing includes a distal portion enclosing said viewing screen and a proximal handle containing said manually actuable device, and said keyswitches are arranged on said distal portion of said control handle housing adjacent said viewing screen.

* * * * *

REEXAMINATION CERTIFICATE (4209th)

United States Patent [19]
Salvati et al.

[11] B1 5,373,317
[45] Certificate Issued Nov. 21, 2000

[54] CONTROL AND DISPLAY SECTION FOR BORESCOPE OR ENDOSCOPE

[75] Inventors: Jon R. Salvati; Fred C. Cope, both of Skaneateles; Dominick Danna, Syracuse; Michael C. Stone, Skaneateles; Raymond A. Lia, Auburn; Gary L. Rink, Jordan; Craig S. Whitaker, Marietta, all of N.Y.

[73] Assignee: Welch Allyn, Inc., Skaneateles, N.Y.

Reexamination Request:
No. 90/005,598, Dec. 23, 1999

Reexamination Certificate for:
Patent No.: 5,373,317
Issued: Dec. 13, 1994
Appl. No.: 08/068,144
Filed: May 28, 1993

[51] Int. Cl.[7] ...................................................... H04N 7/18
[52] U.S. Cl. ................................. 348/65; 348/66; 348/72; 348/76
[58] Field of Search ................................... 348/65, 66, 67, 348/68, 77, 78, 84, 85, 211, 214, 552

[56] References Cited

U.S. PATENT DOCUMENTS

| | | | |
|---|---|---|---|
| 4,503,842 | 3/1985 | Takayama | 128/4 |
| 4,742,819 | 5/1988 | George . | |
| 5,090,259 | 2/1992 | Shishido et al. | 73/623 |
| 5,159,446 | 10/1992 | Hibino et al. | 348/65 |

FOREIGN PATENT DOCUMENTS

| | | |
|---|---|---|
| 63-220831 | 9/1988 | Japan . |
| 1-302216 | 12/1989 | Japan . |

*Primary Examiner*—Andy Rao

[57] ABSTRACT

A control handle and viewing screen assembly combines video monitor and remote steering control for a borescope steering section. A joystick or similar device controls the steering section when an inspection mode is employed. In a second or freeze-frame mode the joystick is used to move a cursor on the screen or to carry out a computation function. Steering servo motors can be positioned distally for balance.

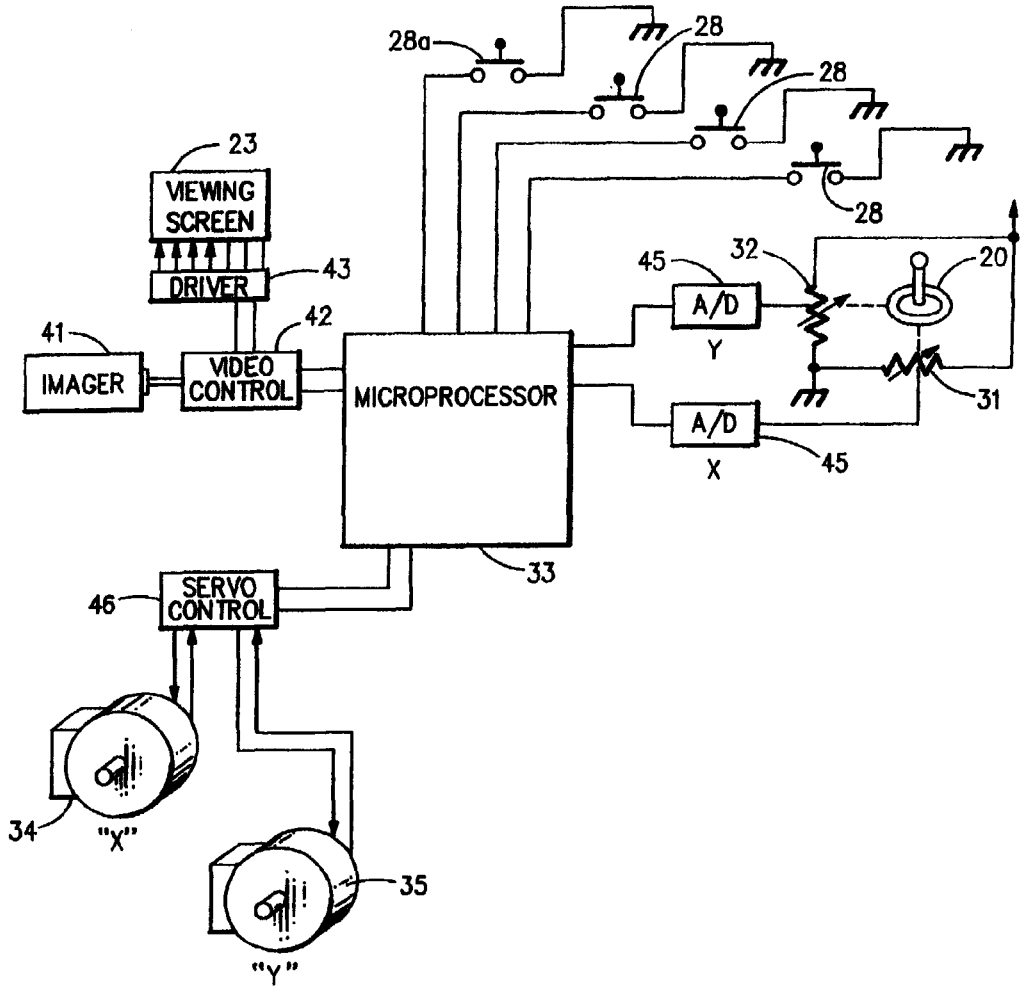

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–18 is confirmed.

* * * * *